United States Patent [19]

Fujikura et al.

[11] Patent Number: 5,039,674
[45] Date of Patent: Aug. 13, 1991

[54] 1,4-DIHYDROPYRIDINE DERIVATIVES

[75] Inventors: Takashi Fujikura, Saitama; Yuzo Matsumoto; Masaharu Asano, both of Tokyo, all of Japan

[73] Assignee: Yamanouchi Pharmaceutical Co., Ltd., Tokyo, Japan

[21] Appl. No.: 463,842

[22] Filed: Jan. 12, 1990

Related U.S. Application Data

[60] Continuation of Ser. No. 216,837, Jul. 8, 1988, abandoned, which is a division of Ser. No. 130,023, Dec. 8, 1987, Pat. No. 4,782,160.

[30] Foreign Application Priority Data

Aug. 12, 1986 [JP] Japan ................................. 292694

[51] Int. Cl.$^5$ .................... C07D 401/10; A61K 31/44
[52] U.S. Cl. .................................... 514/212; 514/255; 514/318; 514/343; 514/356; 514/235.5; 546/321; 546/281; 546/194; 544/131; 544/365; 540/597
[58] Field of Search ........................ 546/321, 281, 194; 544/131, 365; 540/597; 514/255, 318, 343, 356

[56] References Cited

U.S. PATENT DOCUMENTS 3,968,117 7/1976 Bossert et al. ...................... 546/321

Primary Examiner—Jane T. Fan

Attorney, Agent, or Firm—Burgess, Ryan & Wayne

[57] ABSTRACT

Novel 1,4-dihydropyridine derivatives and salts thereof are provided, which can be represented by the formula

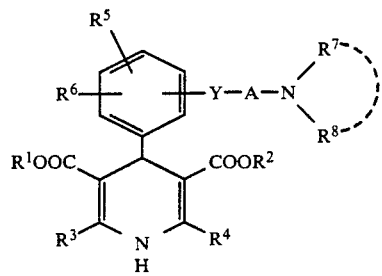

wherein, Y represents an oxygen atom or a sulfur atom; A represents an alkylene group, an alkenylene group or an alkynylene group; and $R^7$ and $R^8$ can represent individual groups or may be combined together with a nitrogen atom(s) to form a pyrrole ring, a piperidine ring, a morpholine ring or a piperazine ring or azepine ring which may be substituted with a lower alkyl group or an aralkyl group. Pharmaceutical compositions containing the derivatives and their use for imparting calcium antagonistic activity are also provided.

3 Claims, No Drawings

1,4-DIHYDROPYRIDINE DERIVATIVES

DETAILED DESCRIPTION OF THE INVENTION

1 Field of the Invention

The present invention relates to novel 1,4-dihydropyridine derivatives represented by general formula (I) described below which are useful as medical drugs, especially as calcium antagonists having excellent durability and salts thereof as well as processes for production thereof.

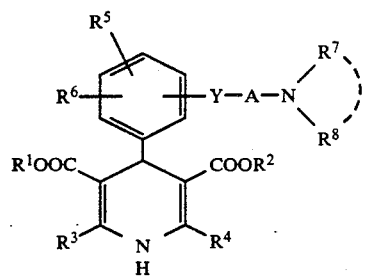

wherein:
R$^1$ and R$^2$: which may be the same or different, each represents an alkyl group which may be intervened by an oxygen atom, a cycloalkyl-substituted lower alkyl group or a halogen-substituted lower alkyl group;

R$^3$ and R$^4$: which may be the same or different, each represents a lower alkyl group;

R$^5$ and R$^6$: which may be the same or different, each represents a hydrogen atom, a nitro group, a halogen atom, a lower alkyl group, a lower alkoxy group, a lower alkylthio group, a lower alkylsulfonyl group or a lower alkylsulfinyl group;

R$^7$: a hydrogen atom or a lower alkyl group;

R$^8$: a lower alkyl group; a hydroxy-lower alkyl group, an aralkyl group, an aryl group, a lower acyl group, a lower alkylsulfonyl group or an aryloxy-lower alkyl group, an aryloxy-lower alkoxy group, provided that R$^7$ and R$^8$ may be combined together with a nitrogen atom(s) to form a pyrrole ring, a piperidine ring, a morpholine ring or a piperadine ring or azepine ring which may be substituted with a lower alkyl group or an aralkyl group;

A: an alkylene group, an alkenylene group or an alkynylene group; and

Y: an oxygen atom or a sulfur atom

2. Prior Art

Since it was confirmed that Nifedipine or Nicardipine exhibits cerebro- and/or coronary vasodilating action based on calcium antagonistic activity, a variety of calcium antagonists containing the 1,4-dihydropyridine skeleton have been extensively developed.

The compounds of the present invention are novel compounds characterized by chemical structure that substituents on the phenyl group at the 4-position thereof are different from these known 1,4-dihydropyridine calcium antagonists and by pharmacological property that durability of calcium antagonistic activity is superior to the known calcium antagonists.

It is disclosed in European Patent Nos. 167, 371 and 194,751 that compounds represented by general formula:

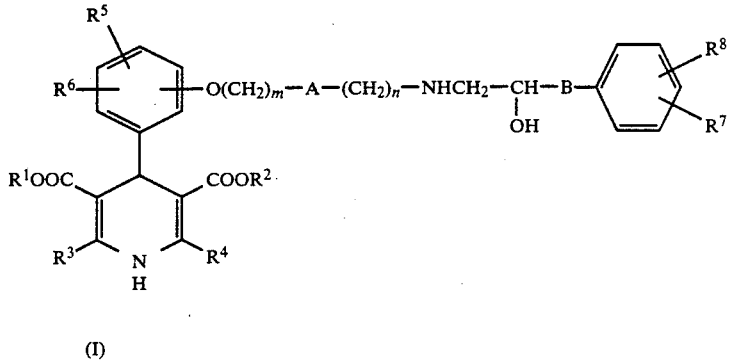

have both calcium receptor antagonistic activity and β-blocking activity. Turning to the present invention, the compounds of the present invention are characterized by lacking β-blocking activity but exhibiting calcium receptor antagonistic activity alone and this activity being durative uncomparatively to conventional compounds.

In addition, it is disclosed in Published Unexamined Japanese Patent Application No. 136558/1985 that compounds represented by general formula:

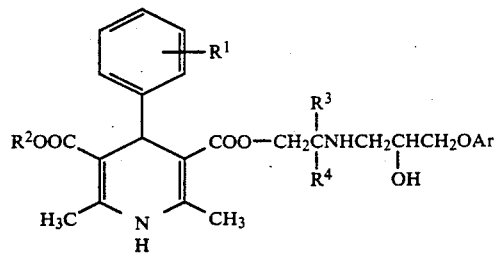

have both calcium receptor antagonistic activity and β-blocking activity. Turning to the present invention, the compounds of the present invention are novel compounds which are different not only in the aforesaid pharmacological property but also in their structure.

MEANS FOR SOLVING THE PROBLEM

The present inventors newly produced various novel compounds of 1,4-dihydropyridine type and as a result of screening compounds of exhibiting calcium antagonistic action having excellent durability, they have found that the compounds represented by general formula (I) described above and salts thereof have particularly remarkable effects and have accomplish the present invention.

Namely, an object of the present invention is to provide the compounds represented by general formula (I)

described above and salts thereof as well as processes for producing the same.

The compounds of the present invention will be described in more detail below.

In the specification, the term "lower" refers to a straight or branched carbon chain having carbon atom numbers of 1 to 6, unless otherwise indicated. Accordingly, concrete examples of the lower alkyl group include methyl group, ethyl group, propyl group, isopropyl group, butyl group, isobutyl group, sec-butyl group, tert-butyl group, pentyl group, isopentyl group, neopentyl group, tert-pentyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, etc.

Further, as the "lower alkoxy group", mention may be made of methoxy group, ethoxy group, propoxy group, isopropoxy group, butoxy group, isobutoxy group, sec-butoxy group, tert-butoxy group, pentyloxy (amyloxy) group, isopentyloxy group, tert-pentyloxy group, neopentyloxy group, 2-methylbutoxy group, 1,2-dimethylpropoxy group, 1-ethylpropoxy group, hexyloxy group, and the like.

The "aryloxy-lower alkoxy group" means a group obtained by substituted an optional hydrogen atom in the aforesaid "lower alkoxy group" with an "aryloxy group" and concrete examples of the "aryloxy group" include phenoxy group, napthyl group and the like, with particular preference of phenoxy group. Accordingly, exemplifying specific "aryloxy-lower alkyl group" by referring to phenoxy group, mention may be made of phenoxymethyl group, phenoxyethyl group, phenoxypropyl group, 1-methyl-2-phenoxyethyl group, phenoxybutyl group, 1-methyl-2-phenoxypropyl group, phenoxypentyl group, phenoxyhexyl. group and the like.

The "lower alkylthio group" refers to a group in which the oxygen atom in the lower alkoxy group described above is replaced with a sulfur atom and specific examples include methylthio group, ethylthio group, propylthio group, isopropylthio group, butylthio group, sec-butylthio group, tert-butylthio group, pentylthio group, neopentylthio group, 2-methbutylthio group, 1,2-dimethylpropylthio group, 1-ethylpropylthio group, hexylthio group, and the like. Further the lower alkylsulfonyl group and the lower alkylsulfinyl group means sulfonyl group and sulfinyl group substituted with the lower alkyl group described above; specific examples are methylsulfonyl (or sulfinyl) group, ethylsulfonyl (or sulfinyl) group, propylsulfonyl or sulfinyl) group, butylsulfonyl (or sulfinyl) group, isobutylsulfonyl (or sulfinyl) group, pentylsulfonyl (or sulfinyl) group, neopentylsulfonyl (or sulfinyl) group, hexylsulfonyl (or sulfinyl) group, and the like.

Further the "cycloalkyl-substituted lower alkyl group" means a group obtained by substituting an optional hydrogen atom in the "lower alkyl group" described above with a "cycloalkyl group" and specific examples of the "cycloalkyl group" are preferably an alicyclic group having 3 to 6 carbon atoms such as cyclopropyl group, cyclobutyl group, cyclopentyl group, cyclohexyl group, etc. Accordingly, concrete examples of the "cycloalkyl-substituted lower alkyl group" are cyclohexylmethyl group, 2-cyclohexylethyl group, 3-cyclohexylpropyl group, 2-cyclohexyl-1-methylethyl group, 4-cyclohexylbutyl group, 5-cyclohexylpentyl group, 6-cyclohexylhexyl group, etc., when shown in terms of cyclohexyl groups.

Further the "halogen-substituted lower alkyl group" means a group obtained by substituting optional 1 to 3 hydrogen atoms in the "lower alkyl group" described above with a "halogen atom"; in this case, as the "halogen atom", preferred are fluorine atom, chlorine atom, bromine atom, etc. Accordingly, in terms of the chlorine atom, concrete examples of the "halogen-substituted lower alkyl group" are chloromethyl group, trichloromethyl group, 2-chloroethyl group, 3-chloropropyl group, 2-chloro-1-methylethyl group, 4-chlorobutyl group, 5-chloropentyl group, 6-chlorohexyl group, and the like.

Further the "hydroxy-lower alkyl group" means a group obtained by substituting an optional hydrogen atom in the "lower alkyl group" described above with a "hydroxy group" and concrete examples are hydroxymethyl group, 2-hydroxyethyl group, 1-hydroxyethyl group, 3-hydroxypropyl group, 2-hydroxypropyl group, 2-hydroxy-2-methylethyl group, 1-hydroxy-2-methylethyl group, 4-hydroxybutyl group, 5-hydroxypentyl group, 6-hydroxyhexyyl group, and the like.

The "arloxy-lower alkyl group" means a group obtained by substituting an optional hydrogen atom in the "lower alkyl group" described above with a "arloxy group" and as the "arloxy group", there are concretely phenoxy group, napthyloxy group, etc., with phenoxy group being particularly preferred. Accordingly, concrete examples of the "arloxy-lower alkyl group" are, in terms of phenoxy group, phenoxymethyl group, phenoxyethyl group, phenoxypropyl group, 1-methyl-2-phenoxyethyl group, phenoxybutyl group, 1-methyl-3-phenoxypropyl group, phenoxypentyl group, phenoxyhexyyl group, and the like.

The "alkyl group which may be intervened by an oxygen atom" includes both "alkyl group" and "alkyl group which may be intervened by an oxygen atom". As the "alkyl group", preferred is a straight or branched group having 1 to 10 carbon atoms. Accordingly, in addition to the concrete examples of the aforesaid "lower alkyl group", concrete examples of the "alkyl group" further include methoxymethyl group, 1-methoxyethyl group, 2-methoxyethyl group, ethoxyethyl group, 3-methoxypropyl group, 2-methoxypropyl group, 2-ethoxyethyl group, methoxybutyl group, methoxypentyl group, ethoxymethyl group, ethoxyethyl group, propoxymethyl group, isopropoxymethyl group, 4-methoxybutyl group, 3-ethoxypropyl group, 2-propoxyethyl group, butoxymethyl group, 5-methoxypentyl group, 4-ethoxybutyl group, 2-(2ethoxyethoxy)ethyl group [3,6-dioxaoctyl group], 2-butoxyethyl group, 2-pentyloxymethyl group, 6-methoxyhexyl group, 5-ethoxypentyl group, 2-pentyloxyethyl group, hexyloxymethyl group, 7-methoxyheptyl group, 6-ethoxyhexyl group, 2-[2(2-ethoxyethoxy)ethoxy]ethyl group [3,6,9-trioxaundecyl group], 2-hexyloxyethyl group, heptyloxymethyl group, 8-methoxyoctyl group, 7-ethoxyheptyl group, 2-heptyloxyethyl group, octyloxymethyl group, 9-methoxynonyl group, and the like.

As the "aryl group", there are concretely phenyl group, naphthyl group and the like but particularly preferred is phenyl group.

The "aralkyl group" means a group obtained by substituting an optional hydrogen atom in the "lower alkyl group" described above with the "aryl group" described above, such as benzyl group, phenethyl group, phenylpropyl group, etc.

As the alkylene group shown by A, preferred is an alkylene group having 1 to 12 carbon atoms. Specific examples are methylene group, ethylene group, methylmethylene group

trimethylene group, propylene group

2-propylene group

dimethylmethylene group

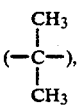

tetramethylene group, 1-methyltrimethylene group, 2-methyltrimethylene group, 3-methyltrimethylene group, 1-ethylethylene group

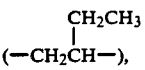

2-ethylethylene group

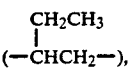

2,2-dimethylethylene group

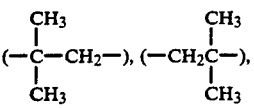

1,1dimethylethylene group
ethylmethylmethylene group

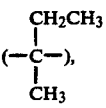

pentamethylene group, 2-methyltetramethylene group, 3-methyltetramethylene group, b 4-methyltetramethylene group, 1,1-dimethyltrimethylene group, 2,2-dimethyltrimethylene group, 3,3-dimethyltrimethylene group, 1,3-dimethyltrimethylene group, 2,3-dimethyltrimethylene group, 1,2-dimethyltrimethylene group, 1-ethyltrimethylene group, 1,1,2-trimethylethylene group, diethylmethylene group, hexamethylene group, 1-methylpentamethylene group, 1,1-dimethyltetramethylene group, 2,2-dimethyltetramethylene group, 3,3-dimethyltetramethylene group, 4,4-dimethyltetramethylene group, 1,1,3-trimethyltrimethylene group, 1,1,2-trimethyltrimethylene group, 1,1,2,2,-tetramethylethylene group, 1,1-dimethyl-2-ethylethylene group, 1,1-diethylethylene group, heptamethylene group, 1-methylhexamethylene group, 1,1-dimethylpentamethylene group, 2,2-dimethylpentamethylene group, 3,3-dimethylpentamethylene group, 4,4-dimethylpentamethylene group, 5,5-dimethylpentamethylene group, 1,1,4-trimethyltetramethylene group, 1,1,2-trimethyltetramethylene group, 1,1,3-trimethyltetramethylene group, 1,1,2,2-tetramethyltrimethylene group, 1,1,3,3-tetrmethyltrimethylene group, 1,1-dimethyl-2-ethyltrimethylene group, 1,1-dimethyl-3-ethyltrimethylene group, octamethylene group, 1-methylheptamethylene group, 1,1-dimethylhexamethylene group, nonamethylene group, 1-methyloctamethylene group, 1,1-dimethylheptamethylene group, decamethylene group, 1-methylnonamethylene group, 1,1-dimethyloctamethylene group, undecamethylene group, 1-methyldecamethylene group, 1,1-dimethylnonamethylene group, dodecamethylene group, 1,1-dimethyldecamethylene group, etc.

Further as the alkenylene group shown by A, preferred as groups having 2 to 12 carbon atoms; concrete examples are vinylene group, propenylene group (—CH$_2$CH=CH—), 2-propenylene group (—CH=—CH$_2$—), 1-methylvinylene group, 2-methylvinylene group, butenylene group, 2-butenylene group, 3-butenylene group, 1-methylpropenylene group, 1-methyl-2-propenylene group, pentenylene group, 1-methylbutenylene group, 1-methyl-2-butenylene group, 1-methyl-3-butenylene group, 1,1-dimethyl-2-propenylene group, hexenylene group, 2-hexenylene group, 3-hexenylene group, 4-hexenylene group, 5-hexenylene group, 1-methyl02-pentenylene group, 1-methyl-3-pentenylene group, 1,1-dimethyl-2-butenylene group, 1,1-dimethyl-3-butenylene group, heptenylene group, 2-heptenylene group, 3-heptenylene group, 4-heptenylene group, 5-heptenylene group, 6-heptenylene group, 1,1-dimethyl-2-pentenylene group, 1,1-diemthyl-3-pentenylene group, 1,1-dimethyl-4-pentenylene group, 2-octenylene group, 4-octenylene group, 7-octenylene group, 1,1-dimethyl-2-hexenylene group, 1,1-dimethyl-3-hexenylene group, 1,1-dimethyl-5-hexenylene group, 2-noneylene group, 2-nonenylene group, 5-nonenylene group, 8-nonenylene group, 1,1-dimethyl-2-heptenylene group, 1,1-dimethyl-3-heptenylene group, 1,1-dimethyl-4-heptenylene group, 1,1-dimethyl-6-heptenylene group, 2-decenylene group, 5-decenylene group, 9-decenylene group, 1,1-dimethyl-4-cotenylene group, 1,1-dimethyl-7-octenylene group, 2-undecenylene group, 5-undecenylene group, 6-undecenylene group, 10-undecenylene group, 1,1-dimethyl-2-nonenylene group, 1,1-dimethyl-4-nonenylene group, 1,1-dimethyl-5-nonenylene group, 1,1-dimethyl-8-nonenylene group, 2-dodecenylene group, 6-dodecenylene group, 11-dodecenylene group, 1,1-dimethyl-2-dodecenylene group, 1,1-dimethyl-5-dodecenylene group, 1,1-dimethyl-9-dodecenylene group, etc.

Further as the alkynylene group shown by A, preferred is group having 2 to 12 carbon atoms and there are concretely ethynylene group, propynylene group (—CH$_2$—C≡C—), 2-propynylene group (—C≡

C—CH$_2$—), butynylene group, 2-butynylene group, 3-butynylene group, 1-methyl-2-propynylene group, pentynylene group, 2-pentynylene group, 3-pentynylene group, 4-pentynylene group, 3-methylbutynylene group, 4-methylbutynylene group

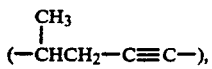

1-methyl-2-butynylene group, 4-methyl-2-butynylene group, 1,1-dimethyl-2-propynylene group

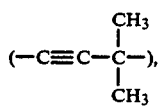

hexynylene group, 2-hexynylene group, 3-hexynylene group, 4-hexynylene group, 5-hexynylene group, 1-methyl-3-pentynylene group, 1-methyl-4-pentynylene group, 1,1-dimethyl-2-butynylene group, 1,1-dimethyl-3-butynylene group, heptynylene group, 2-heptynylene group, 3-heptynylene group, 4-heptynylene group, 5-heptynylene group, 6-heptynylene group, 1,1-dimethyl-2-pentynylene group, 1,1-dimethyl-4-pentynylene group, 2-octynylene group, 1,1-dimethyl-2-hexynylene group, 1,1-dimethyl-3-hexynylene group, 1,1-dimethyl-5-hexynylene group, 4-nonynylene group, 5-nonynylene group, 8-nonynylene group, 1,1-dimethyl-2-heptynylene group, 1,1dimethyl-3-heptynylene group, 1,1-dimethyl-4-heptynylene group, 1,1-dimethyl-6-heptynylene group, 2-decynylene group, 5-decynylene group, 9-decynylene group, 1,1-dimethyl-2-octynylene group, 1,1-dimethyl-4-octynylene group, 1,1-dimethyl-7-cotynylene group, 2-undecynylene group, 5-undecynylene group, 6-undecynylene group, 10-undecynylene group, 1,1-dimethyl-2-nonynylene group, 1,1-dimethyl-4-nonynylene group, 1,1-dimethyl-5-nonynylene group, 1,1-dimethyl-8-nonynylene group, 2-dodecynylene group, 6-dodecynylene group, 11-dodecynylene group, 1,1-dimethyl-2-dodecynylene group, 1,1-dimethyl-5-dodecynylene group, 1,1-dimethyl-9-dodceynylene group, etc.

The compounds represented by general formula (I) forms salts thereof.

The present invention includes the salts of compounds (I), and examples of such salts include acid addition salts with inorganic acids such as minerla acids, e.g., hydrochloric acid, hydrobromic acid, hydroiodic acid, sulfuric acid, nitric acid, phosphoric acid or the like and, with various organic acids such as formic acid, acetic acid, oxalic acid, citric acid, succinic acid, fumaric acid, maleic acid, malic acid, tartaric acid, methanesulfonic acid, ethanesulfonic acid or the like.

In addition, in the case of containing asymmetric carbon atoms at the 4-position of the dihydropyridine ring or depending upon kinds of the substituent at the 4-position of the phenyl group, the compounds of the present invention may contain additional asymmetric carbon atoms and further include compounds having double bonds; in these compounds, various isomers such as optical isomers, diastereoisomers and geometrical isomers or the like may be present.

The present invention includes isolated products of such optical and stereoisomers and a mixture thereof.

The present invention also includes processes of producing the compounds represented by general formula (I). The compounds (I) of the present invention can be prepared by various processes. Representative examples of the processes will be given below.

Process 1:

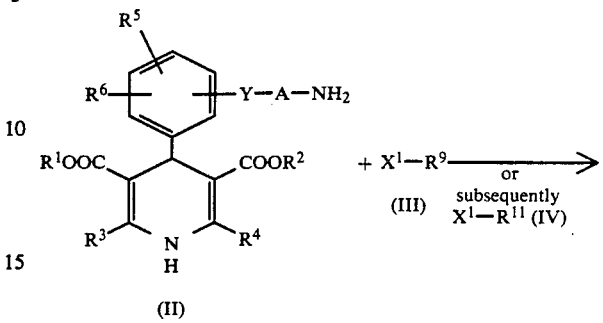

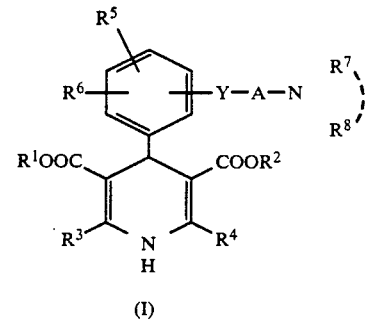

wherein $R^1$, $R^2$, $R^3$, $R^4$, $R^5$, $R^6$, $R^7$, $R^8$ and A have the same meanings as described above; $R^9$ represents a lower alkyl group, a hydroxy-lower alkyl group, an aralkyl group, an aryl group, a lower acyl group, a lower alkylsulfonyl group, an aryloxy-lower alkyl group, an aryloxy-lower alkoxy group or a group shown by formula:

$X^1$ represents a halogen atom, an organic sulfonic acid residue or a lower acyloxy group; B represents tetramethylene group, pentamethylene group, hexamethylene group, 3-oxapentamethylene group (—CH$_2$CH$_2$OCH$_2$CH$_2$—) or a group shown by formula:

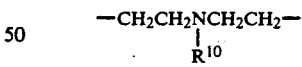

$X^2$ represents the same or different halogen atom when $X^1$ represents a halogen atom; $R^{10}$ represents a hydrogen atom, a lower alkyl group or an aralkyl group; and $R^{11}$ represents a lower alkyl group.

Herein as the halogen atom, mention may be made of iodine atom, bromine atom, chlorine atom, etc. Further examples of the organic sulfonic acid residue are an alkanesulfonic acid residue such as methanesulfonyloxy group, ethanesulfonyloxy group and the like; an aromatic sulfonic acid residue such as benzenesulfonyloxy group, toluene (in particular, p-toluene)sulfonyloxy group and the like. As the lower acyloxy group, mention may be made of acetoxy, propionyloxy, etc.

The compounds (I) of the present invention can be produced by;

(1) reacting amines represented by general formula (II) with halides, acid anhydrides or sulfonates represented by general formula (III), or;
(2) reacting halides, acid anhydrides or sulfonates represented by general formula (IV) with secondary amines obtained in (1).

When the compounds (III) is $-X^1-B-X^2$, $X^1$ and $X^2$ are both halogen atoms, with the same halogen atom being particularly preferred.

The reactions (1) and (2) described above can both be carried out under similar reaction conditions and will be described in detail, dividing into cases wherein $X^1$ represents a halogen atom or a lower acyloxy group and represents an organic sulfonic acid residue.

The reaction using as starting compounds (III) compounds wherein $X^1$ represents a halogen atom or a lower acyloxy group, can proceed also in the absence of any solvent but it is generally advantageous to conduct the reaction in organic solvents such as benzene, toluene, xylene, dimethylformamide, dimethylsulfoxide, acetonitrile, dichloromethane, dichloroethane, etc.

The amounts of starting compounds are that the compounds (II) and (III) are used in almost equimolar amounts or the compounds (III) are used in a slightly excess amount.

The reaction is preferably conducted at room temperature or with heating or with heating under reflux.

Upon this reaction, it is sometimes advantageous to add secondary or tertiary bases such as pyridine, picoline, N,N-dimethylaniline, N-methylmorpholine, trimethylamine, triethylamine, dimethylamine, or the like; or inorganic bases such as potassium carbonate, sodium carbonate, sodium hydrogencarbonate, or the like, in order to smoothly proceed the reaction.

Further in order to prevent the side reaction, it is also possible to introduce a protective group into the amino group of the compounds (II), perform the reaction and splitting the protective group off after the reaction. As such a protective group, mention may be made of toluenesulfonyl group, acetyl group, phenacylsulfonyl group, trifluoromethanesulfonyl group, bisbenzenesulfonyl group, etc. Splitting the protective group off can be easily achieved by conventional hydrolysis using acids or bases.

The reaction using the compounds substituted with organic sulfonic acid residues as the starting compounds (III) can be advantageously carried out by reacting the compounds (II) with the compounds (III) in an equimolar amount or in an excess amount of the compounds (III) in an organic solvent inert to the reaction such as methanol, ethanol, toluene, tetrahydrofuran, etc., under cooling or at room temperature. Taking various reaction conditions into account, the reaction time can be appropriately set.

In order to produce asymmetric amines, the compounds (V) are then reacted with the secondary amines obtained in the reaction described above.

The reaction conditions and procedures are similar to those described above.

Process 2:

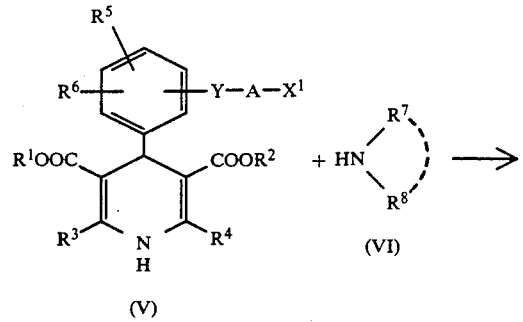

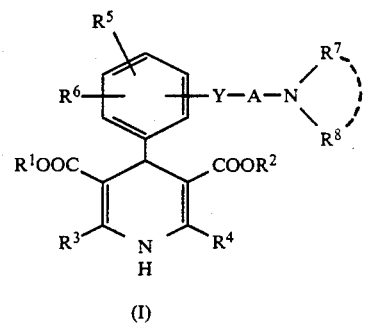

wherein $R^1$, $R^2$, $R^3$, $R^4$, $R^5$, $R^6$, $R^7$, $R^8$, A and $X^{10}$ have the same meanings as described above.

The compounds (I) of the present invention can also be produced by reacting halides or sulfonates represented by general formula (V) with amines represented by general formula (VI).

The reaction is almost similar to the N-alkylation in Process 1.

Process 3:

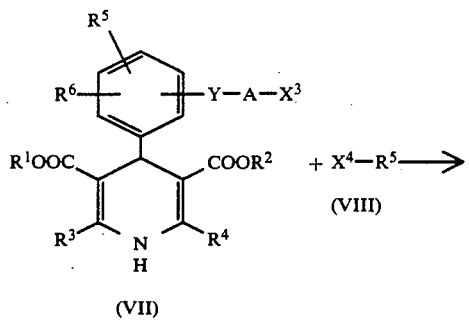

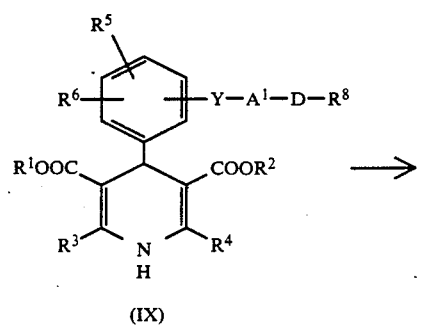

-continued

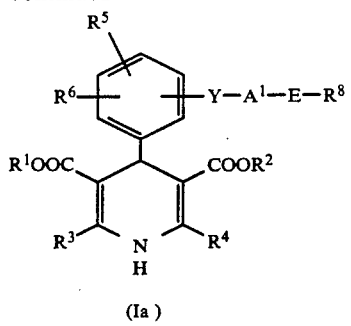

(Ia)

wherein $R^1$, $R^2$, $R^3$, $R^4$, $R^6$ and $R^8$ have the same meanings as described above; and other symbols have the following meanings:

$A^1$: A or an alkylene group having carbon atoms less than those of A by 1 carbon atom, an alkenylene group or an alkynylene group $X^3$ and $X^4$: one is formyl group and another is an amino group D: a group shown by formula: —CH=N— or —N=CH—

E: a group shown by formula: —CH$_2$NH— or —NHCH$_2$—.

The compounds represented by general formula (Ia) can be produced by reacting aldehydes or amines represented by general formula (VII) with amines or aldehydes represented by general formula (VIII) and then reductive condensation of reducing the resulting Schiff's bases (IX) under conditions that the nitro group is not reduced.

The reaction at the former stage can also proceed in the absence of any solvent but generally carried out using equimolar amounts of the compounds (VII) and the compounds (VIII) or an excess amount of either compound at room temperature or with heating or with heating under reflux in an organic solvent inert to the reaction such as alcohols, e.g., methanol, ethanol or the like, or benzene, etc. Depending upon the reaction conditions, in some occasion, it may be advantageous to incorporate potassium hydroxide or remove the released water using Dean-Stark trap.

In the reduction, the reducing agent can also be added to the reaction solution containing the Schiff's bases to perform the reaction, without isolating the Schiff's bases.

Further in order to produce the compounds (Ia) of the present invention by selectively reducing the imino group alone in the Schiff's bases without reducing the nitro group, it is advantageous to use as the reducing agent a borohydride such as sodium borohydride, lithium borohydride, sodium cyanoborohydride, etc.

The reduction is carried out in an organic solvent such as an alcohol, e.g., methanol, ethanol or the like, acetic acid, etc., water or a solvent mixture thereof, generally at room temperature or with heating.

Upon the reaction, it is sometimes advantageous to maintain the property of the reaction solution in a neutral or basic region, for purposes of smoothly proceeding the reaction; if necessary, methylamine, ethylamine, propylemine, dimethylamine, potassium hydroxide, sodium acetate, or the like are incorporated to perform the reaction.

OTHER PROCESSES

As above, the processes in which attention is brought only to the amine moiety in the substituted aminoalkoxy group substituted on the phenyl group at the 4-position thereof are disclosed herein. However, the compounds (I) of the present invention contain not only various functional groups therein but also the dihydropyridine skeleton. The compounds can also be produced by synthesis methods, bringing attention to each functional group, or by synthesis method of the 1,4-dihydropyridine skeleton (Hantzsch's synthesis method).

The thus produced compounds of the present invention an be used as they are in a free state or isolated as salts thereof and purified. Isolation and purification are performed by applying conventional chemical operations such as extraction, crystallization, recrystallization, various chromatography techniques, etc.

In the compounds of the present invention, isomers such as racemi isomers, optically active forms, diastereomers and the like are present singly or as admixture thereof. The racemi compounds can be led to stereochemically pure isomers by using appropriate raw compounds or by conventional racemi resolution [for example, they are led to the diastereomer with a conventional optically active acid (tartaric acid, etc.) followed by optical resolution, etc.]. Further the mixture of diastereomers can be spearated in a conventional manner, for example, fractional crystallization or chromatography, etc.

EFFECTS OF THE INVENTION

The compounds (I) and salts thereof provided by the present invention possess a calcium antagonistic action having excellent durability.

These pharmacological effects of these compounds of the present invention have been confirmed by the following test method. With respect to hypotensive effect and coronary blood flow increasing effect, the compounds are effective in a range of 0.01 to 1 mg/kg by intravenous administration and with respect to coronary vasodilating action by administration in the coronary artery, in a range of 1to 300 μg. In addition, reduced working load on the heart and decrease in oxygen consumption of the heart muscle were noted. It has also been confirmed that the duration time of the pharmacological effects is longer than known dihydropyridine compounds.

Hereafter with regard to major compounds out of the compounds of the present invention, test methods and results for supporting these effects are described below (before the Examples portion).

Accordingly the compounds (I) of the present invention and salts thereof show vasodilatory actions in the body blood vessels and the coronary artery based on the calcium antagonistic action and are useful as agents for prophylaxis and treatment of ischemic heart disorders such as angine pectoris, myocardial infarction, etc. as well as circulatory diseases such as hypertension, arrhythmia, etc., as side effects being minimized as compared to known dihydropyridine calcium antagonists and as being applicable in less administration time. Further, the compounds of the present invention also have an action of improving cerebro-vascular contraction and an action of improving central functions, in addition to the circulatory action and are also useful as agents of improving cerebro-vascular contraction and agents of improving central functions.

Preparatory compositions containing one or more compounds represented by general formula (I) or salts thereof as effective components can be prepared into tablets, powders, granules, granulates, capsules, pills, liquid, injections, suppositories, ointments, haps, etc. using carriers, excipients, etc. for medical preparations conventionally used and other additives, and administered orally (including sublingual administration) or parenterally.

The carriers and excipients for medical preparations include solid or liquid non-toxic pharmaceutical substances. Examples of such substances are lactose, magnesium stearate, starch, talc, gelatin, agar, pectin, gum arabic, olive oil, sesami oil, cacao butter, ethylene glycol, etc. and other substances ordinarily used.

Clinical dosage of the compounds of the present invention may be appropriately determined depending upon condition, body weight, age, sex, etc. of the patient to be administered, but is generally 50 to 200 mg daily for adult, which is administered one or twice daily.

METHOD

1 $Ca^{2+}$-Antagonistic Activity $Ca^{2+}$-Antagonistic activity of the compound was evaluated in [$^3$H]-nitrendipine ([$^3$H]-NIT) binding assay. The inhibitory effect of the test compound on [$^3$H]-NIT binding to rat brain membranes was evaluated according to the method of Gould, Murphy and Snyder ([$^3$H]-Nitrendipine-labeled calcium channels discriminate inorganic calcium agonists and antagonists. (Proc. Nati. Acad, Sci. USA., 79, 3656–3660, 1982). The $IC_{50}$ values, the concentration required to inhibit specific binding by 50%, were computed by logit-log analysis and then the inhibition constant ($K_i$ value in nM) was obtained (Table 1).

TABLE 1

Effect on [$^3$H]-nitrendipine binding in rat brain membrane preparations.

| Compound | Ki (nM) | Hill coefficient |
|---|---|---|
| Example 1 | 75 (60–95) | 1.04 |
| Nifedipine | 4.6 (4.2–5.2) | 1.10 |

Value are the mean of 3 experiments. Figures in parenthesis represent 95% confidence limits.

2 Hypotensive Activity

The effect of the compound on arterial blood pressure (systolic, SBP mean, MPB diastolic, DBP) and hear rate (HR) was evaluated in conscious normotensive rats (NTR). Four to six days before the experiments, a polyethylene catheter for recording arterial blood pressure was surgically implanted into the thoracic aorta via the carotid artery under ehter anesthesia. Arterial blood pressure and heart rate were recorded under freely moving conditions. The test compounds were suspended in 0.5% methylcelluose solution and administered by oral gavage.

Table 2 summarizes the changes in HR, SBP, MBP and DBP of conscious NTR after oral administration of the test compounds.

TABLE 2

Effect of oral administration of the Example 1 compound (30 mg/kg) on heart rate (HR), systolic blood pressure (SBP), mean blood pressure (MBP) and diastolic blood pressure (DBP) in cannulated conscious normotensive rats.
Value are the mean ± S.E.M. of 6 rats.
30 mg/kg p.o. (n = 6)
the Example 1 compound

| Parameter | Initial Value | Change (Δ) Time after oral administration (hr) | | | | | | | | |
|---|---|---|---|---|---|---|---|---|---|---|
| | | 1 | 2 | 3 | 4 | 5 | 6 | 8 | 10 | 24 |
| HR | 361 | 43.0** | 77.8** | 62.2** | 55.0** | 55.3** | 30.5* | 33.0 | 22.5 | 28.0 |
| (beats/min) | ±7.7 | ±9.9 | ±11.7 | ±11.6 | ±10.7 | ±12.6 | ±11.6 | ±14.1 | ±14.1 | ±19.1 |
| SBP | 137 | −10.2 | −17.2* | −24.3* | −18.7** | −16.2* | −16.8* | −15.3** | −14.7** | 0.7 |
| (mm Hg) | ±3.7 | ±4.3 | ±6.5 | ±6.7 | ±4.6 | ±4.4 | ±5.0 | ±2.9 | ±2.1 | 2.1 |
| MBP | 114 | −12.1* | −20.0* | −25.1** | −18.9** | −16.5** | −14.4* | −13.5** | −13.1** | 0.7 |
| (mm Hg) | ±3.6 | ±4.1 | ±5.4 | ±5.2 | ±3.6 | ±3.3 | ±4.1 | ±2.1 | ±1.9 | 2.2 |
| DBP | 103 | −13.0* | −21.3** | −25.5** | −19.0** | −16.7** | −13.2* | −12.5** | −12.3** | 0.7 |
| (mm Hg) | ±3.6 | ±4.0 | ±4.9 | ±4.4 | ±3.3 | ±3.0 | ±3.7 | ±1.8 | ±2.1 | 2.3 |

Effect of oral administration of nifedipine (3 mg/kg) on heart rate (HR), systolic blood pressure (SBP), mean blood pressure (MBP) and diastolic blood pressure (DBP) in cannulated conscious mormotensive rats.
Value are the mean ± S.E.M. of 8 rats.
Nifedipine 3 mg/kg p.o. (n = 8)

| Parameter | Initial Value | Change (Δ) Time after oral administration (hr) | | | | | | | |
|---|---|---|---|---|---|---|---|---|---|
| | | 0.25 | 0.5 | 0.75 | 1 | 1.5 | 2 | 3 | 4 |
| HR | 349 | 77.4** | 51.6** | 35.4* | 23.0 | 12.9 | 2.3 | −20.3 | −13.4 |
| (beats/min) | ±6.9 | ±11.9 | ±11.2 | ±14.8 | ±18.3 | ±14.4 | ±16.7 | ±11.4 | ±13.7 |
| SBP | 136 | −14.4* | −17.6** | −18.1** | −17.0** | −11.0** | −10.4* | −5.4 | −0.3 |
| (mm Hg) | ±2.2 | ±4.4 | ±4.4 | ±3.9 | ±2.7 | ±2.9 | ±3.1 | ±4.5 | ±3.6 |
| MBP | 110 | −18.7** | −19.1** | −19.5** | −18.3** | −11.5** | −9.7* | −3.5 | 0.5 |
| (mm Hg) | ±1.8 | ±3.5 | ±2.9 | ±2.1 | ±1.6 | ±2.9 | ±2.9 | ±4.4 | ±3.5 |
| DBP | 97 | −20.9** | −19.9** | −20.1** | −18.9** | −11.8** | −9.4* | −2.6 | 0.9 |
| (mm Hg) | ±1.8 | ±3.2 | ±2.5 | ±1.9 | ±1.6 | ±3.0 | ±3.0 | ±4.4 | ±3.6 |

Significantly different from initial value (* p <0.05, ** p <0.01 paired t-test).

3 Acute Toxicity

Acute toxicity of the test compound was evaluated according to the method of Brownless, Hodges and Rosenblatt (The Up and Down Method with Small Samples. J. Am. Stat. As., 48, 262–277, 1953). The $ID_{50}$ value of the test compound after intravenous injection to ICR-SLC mice was obtained (Table 3).

TABLE 3

| Compound | Acute toxicity in mice | |
|---|---|---|
|  | n | LD$_{50}$ (mg/kg i.v.) |
| Example 1 | 10 | 29.0 |
| Verapamil | 10 | 10.3 |

EXAMPLE 1

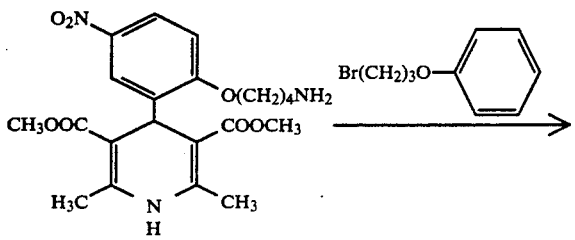

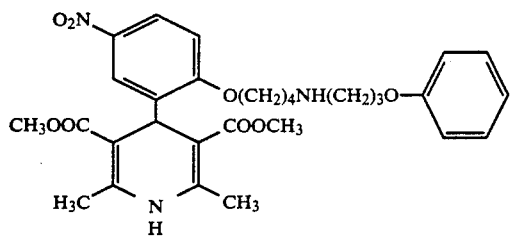

In 20 ml of N,N-dimethylformamide was dissolved 1 g of dimethyl 4-[2-(4-aminobutoxy)-5-nitrophenyl]-2,6-dimethyl-1,4-dihydropyridine-3,5-dicarboxylate. The solution was heated at 100° C. for 1.5 hours. The reaction solution was carefully poured onto 500 ml of ice water. The precipitated oily substance was extracted with ethyl acetate. After drying over anhydrous sodium sulfate, the solvent was removed by distillation under reduced pressure. The obtained residue was subjected to silica gel column chromatography and eluted by chlorform:methanol (96:4 v/v). The obtained crude crystals were recrystallized form ethanol to give 1.2 g of dimethyl 4-[2-[4-(3-phenoxypropylamino)butoxy]-5-nitrophenyl]-2,6-dimethyl-1,4-dihydropyridine-3,5-dicarboxylate. This compound has the following physicochemical properties.

(i) Melting point: 128°–130° C.

| (ii) Elemental analysis (as C$_{30}$H$_{37}$N$_3$O$_8$.H$_2$O) | | | |
|---|---|---|---|
|  | C (%) | H (%) | N (%) |
| Calcd. | 61.53 | 6.71 | 7.17 |
| Found | 61.42 | 6.45 | 7.00 |

EXAMPLE 2

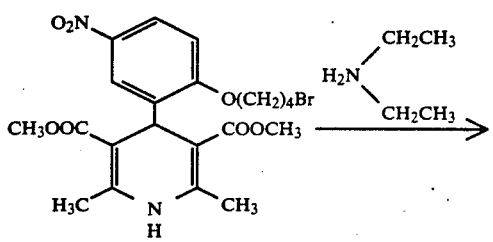

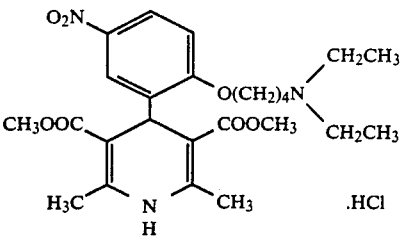

In 30 ml of acetonitrile were dissolved 3 g of dimethyl 4-[2-(4-bromobutoxy)-5-nitrophenyl]-2,6-dimethyl-1,4-dihydropyridine-3,5-dicarboxylate and 0.88 g of diethylamine. The solution was heated to rflux for 2.5 hours. The reaction solution was carefully poured onto 500 ml of ice water. The solvent was removed by distillation under reduced pressure. The obtained residue was dissolved in methylene chloride followed by washing with 10% sodium hydroxide aqueous solution and then with 1N hydrochloride. The solvent was removed from the organic phase by distillation under reduced pressure. The obtained crude crystals were recrystallized from methanol-ethanol to give 1.3 g of dimethyl 4-[2-(4-diethylaminobutoxy]-5-nitrophenyl]-2,6-dimethyl-1,4-dihydropyridine-3,5-dicarboxylate hydrochloride. This compound has the following physicochemical properties.

(i) Melting point: 216°–219° C.

| (ii) Elemental analysis (as C$_{25}$H$_{36}$N$_3$O$_7$Cl.0.3H$_2$O) | | | |
|---|---|---|---|
|  | C (%) | H (%) | N (%) | Cl (%) |
| Calcd. | 56.50 | 6.94 | 7.91 | 6.67 |
| Found | 56.49 | 6.84 | 7.71 | 6.40 |

(iii) Nuclear magnetic resonance (DMSO-d$_6$)
δ:1.26 (6H, t); 1.7–2.0 (4H, m); 2,29 (6H, s); 3.52 (6H, s); 4.0–4.2 (2H, m); 5.21 (1H, s); 7.12 (1H, d); 7.9–8.1 (2H, m); 9.21 (1H, s).

EXAMPLES 3 TO 8

The following compounds were obtained in a similar manner.

EXAMPLE 3

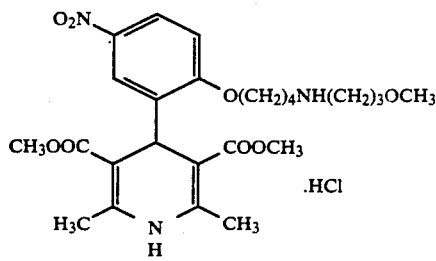

Dimethyl 4-[2-(4-butylaminobutoxy)-5-nitrophenyl]-2,6-dimethyl-1,4-dihydropyridine-3,5-dicarboxylate hydrochloride Physicochemical Properties (i) Melting point: 220°–222° C.

| (ii) Elemental analysis (as $C_{25}H_{36}N_3O_7Cl$) | | | | |
|---|---|---|---|---|
| | C (%) | H (%) | N (%) | Cl (%) |
| Calcd. | 57.08 | 6.90 | 7.99 | 6.74 |
| Found | 56.79 | 6.80 | 7.86 | 6.49 |

(iii) Nuclear magnetic resonance (DMSO-$d_6$)
δ: 0.91 (3H, t); 5.20 (1H, s);
2.28 (6H, s); 7.13 (1H, d); 2.8-3.1 (4H, m); 7.95-8.10 (2H, m);
3.5 (6H, s); 9.26 (1H, s);
4.0-4.2 (2H, m).

EXAMPLE 4

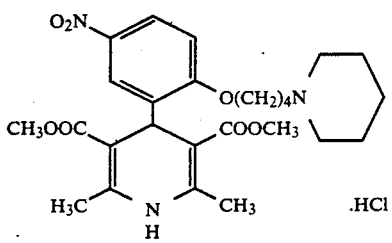

Dimethyl 4-[2-[4-(1-piperidino)butoxy]-5-nitrophenyl]-2,6-dimethyl-1,4-dihydropyridine-3,5-dicarboxylate hydrochloride Physicochemical Properties (i) Melting point: 214°-218° C.

| (ii) Elemental analysis (as $C_{26}H_{36}N_3O_7Cl\cdot0.3H_2O$) | | | | |
|---|---|---|---|---|
| | C (%) | H (%) | N (%) | Cl (%) |
| Calcd. | 57.46 | 6.79 | 7.73 | 6.52 |
| Found | 57.44 | 6.70 | 7.71 | 6.65 |

(iii) Nuclear magnetic resonance (DMSO-$d_6$)
δ:1.6-2.0 (8H, m); 5.19 (1H, s);
2.24 (6H, s); 7.09 (1H, d);
3.47 (6H, s); 7.9-8.1 (2H, m);
4.0-4.2 (2H, m); 9.17 (1H, s).

EXAMPLE 5

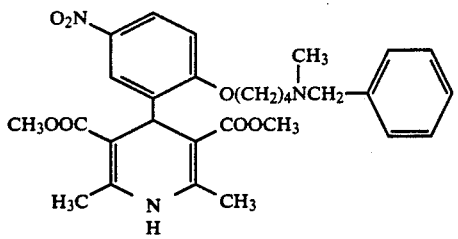

Dimethyl 4-[2-[4-(N-benzyl-N-methylaminobutoxy)butoxy]-5-nitrophenyl]-2,6-dimethyl-1,4-dihydropyridine-3,5-dicarboxylate Physicochemical Properties (i) Melting point: 73°-74° C.

| (ii) Elemental analysis (as $C_{29}H_{35}N_3O_7$) | | | |
|---|---|---|---|
| | C (%) | H (%) | N (%) |
| Calcd. | 64.79 | 6.56 | 7.82 |
| Found | 64.63 | 6.69 | 7.83 |

(iii) Nuclear magnetic resonance (CDCl$_3$)
δ: 1.5-2.1 (4H, m); 3.58 (6H, s);
2.26 (3H, s); 4.04 (2H, t);
2.30 (6H, s); 5.34 (1H, s);
2.46 (2H, t); 6.82 (1H, d);
3.52 (2H, s); 7.2-7.4 (5H, m);
7.9-8.2 (2H, m).

EXAMPLE 6

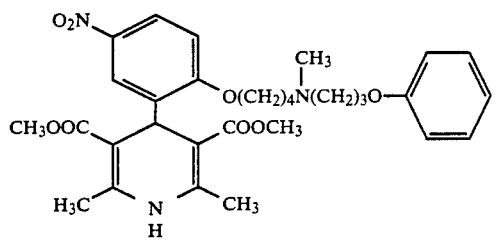

Dimethyl 4-[5-nitro-2-[4-[N-methyl-N-(3-phenoxypropyl)-amino]butoxy]phenyl]-2,6-dimethyl-1,4-dihydropyridine-3,5-dicarboxylate Physicochemical Properties (i) Melting point: 176°-179° C.

| (ii) Elemental analysis (as $C_{31}H_{39}N_3O_8$) | | | |
|---|---|---|---|
| | C (%) | H (%) | N (%) |
| Calcd. | 64.01 | 6.76 | 7.22 |
| Found | 63.89 | 6.64 | 7.32 |

(iii) Nuclear magnetic resonance (CDCl$_3$)
δ:1.8-2.4 (6H, m); 3.9-4.2 (4H, m);
2.34 (6H, s); 5.32 (1H, s);
2.52 (3H, s); 6.7-7.1 (4H, m);
2.7-3.0 (4H, m); 7.2-7.4 (2H, m);
3.58 (2H, s); 7.9-8.2 (2H, m).

EXAMPLE 7

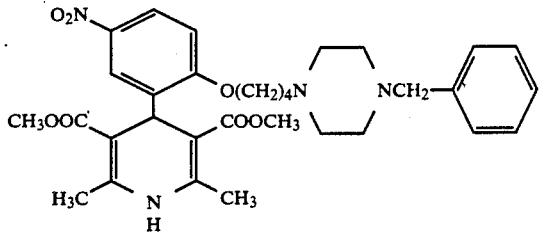

Dimethyl 4-[2-[4-(4-benzyl-1-piperazinyl)butoxy)-5-nitrophenyl]-2,6-dimethyl-1,4-dihydropyridine-3,5-dicarboxylate Physicochemical Properties (i) Melting point: 81°-83° C.

| (ii) Elemental analysis (as $C_{32}H_{40}N_4O_7$) | | | |
|---|---|---|---|
| | C (%) | H (%) | N (%) |
| Calcd. | 64.85 | 6.80 | 9.45 |
| Found | 64.41 | 6.72 | 9.49 |

(iii) Nuclear magnetic resonance ($CDCl_3$)
δ:1.4–2.1 (8H, m); 4.02 (2H, t);
2.28 (6H, s); 5.26 (1H, s);
2.6–2.9 (2H, m); 6.82 (1H, d);
3.52 (2H, s); 7.2–7.4 (5H, m);
3.56 (6H, s); 7.9–8.2 (2H, m).

EXAMPLE 8

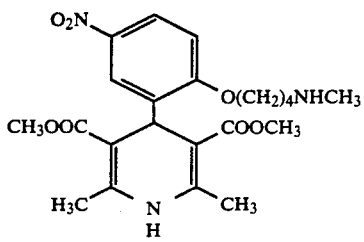

Dimethyl 4-[2-[4-(N-methylamino)butoxy]-5-nitrophenyl]-2,6-dimethyl-1,4-dihydropyridine-3,5-dicarboxylate
Physicochemical properties (i) Melting point: 167°–169° C.

| (ii) Elemental analysis (as $C_{22}H_{29}N_3O_7$) | | | |
|---|---|---|---|
| | C (%) | H (%) | N (%) |
| Calcd. | 59.05 | 6.53 | 9.39 |
| Found | 58.78 | 6.62 | 9.28 |

(iii) Nuclear magnetic resonance ($CDCl_3$)
δ: 1.5–2.1 (4H, m); 4.04 (2H, t);
2.30 (6H, s); 5.28 (1H, s);
2.48 (3H, s); 6.82 (1H, d);
2.72 (2H, t); 7.9–8.2 (2H, m);
3.56 (6H, s).

REFERENCE EXAMPLE 1

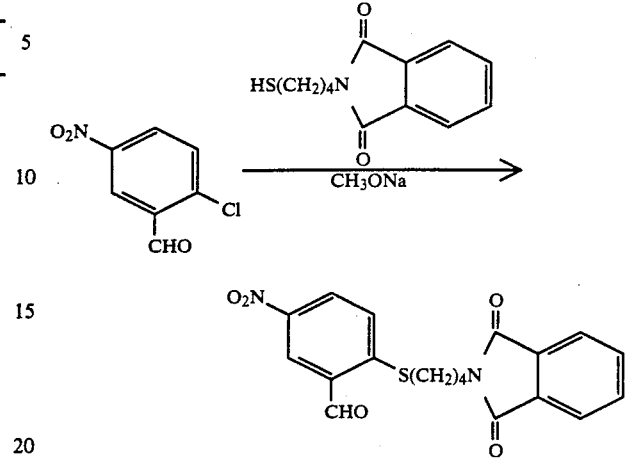

In 40 ml of methanol was dissolved 0.7 g of metallic sodium. A solution of 7.16 g of 4-phthalimido-butylthiol was added to the solution followed by stirring at room temperature for 15 mintues. The, 4.64 g of 2-chloro-5-nitrobenzaldehyde was added to the reaction mixture, which was heated to reflux for 6 hours. After the solvent was removed by distillation under reduced pressure, 15 ml of methanol was added to the residue and the precipitates were taken out by filtration. The precipitates were washed with water and methanol to give 3.94 g of 5-nitro-2-(4-phthalimidobutylthio)benzaldehyde.

Nuclear magnetic resonance (DMSO-$d_6$)
δ:1.5–2.0 (4H, m); 3.16 (2H, t);
3.64 (2H, t); 7.70 (1H, d);
7.86 (4H, bs); 8.32 (1H, d);
8.70 (1H, d); 10.16 (1H, s).

REFERENCE EXAMPLE 2

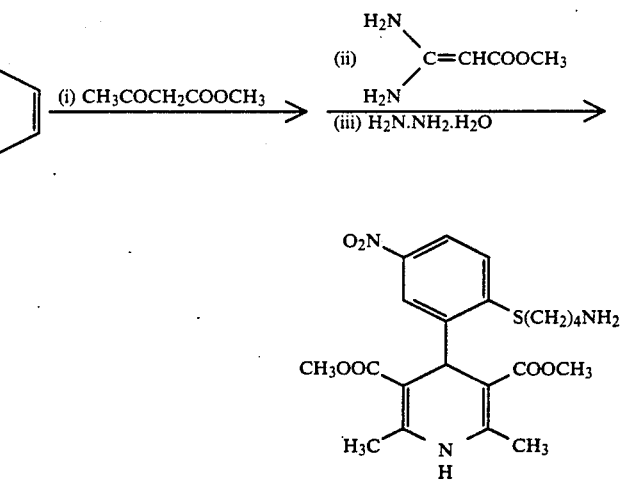

(1) To 4 g of 5-nitro-2-(4-phthalimidobutylthio)benzaldehyde were added 100 ml of benzene, 1.21 g of methyl acetoacetate, 0.04 ml of piperidine and 0.12 ml of acetic acid. The mixture was heated to reflux for 4 hours using Dien-Stalk device. After cooling, the reaction mixture was washed twice with saturated sodium hydrogencarbonate aqueous solution and 2N hydrochloric acid, respectively. After drying over anhydrous sodium sulfate, the solvent was removed by distillation under reduced pressure to give an oily substance. Ether was added to the oily substance to solidify the oil. Thus, 4.9 g of the solid was obtained. The solid was used in a subsequent step without purification.

(2) To 4.9 g of the solid obtained above were added 49 ml of isopropyl alcohol and 1.17 g of methyl 3-aminocrotonate. The mixture was heated to reflux overnight. To the reaction solution were added 100 ml of ethanol and 6.38 g of hydrated hydrazine followed by heating to reflux for an hour. After cooling, insoluble matters were filtered off and the solvent was removed by distillation under reduced pressure. To the residue were added 80 ml of ethyl acetate and 80 ml of water, which was fractionated. After drying the organic phase over anhydrous sodium sulfate, the solvent was removed by distillation unde reduced pressure. Ether was added to the residue to crystallize and give 3.4 g of dimethyl 4-[2-(4-aminobuthylthio-5-nitrophenyl]-2,6-dimethyl-1,4-dihydropyridine-3,5-dicarboxylate. This compound has the following physicochemical properties.

(i) Melting point: 260° C. (decomposed)
(ii) Nuclear magnetic resonance (DMSO-$d_6$)
δ: 1.4–2.00 (4H, m); 2.24 (6H, s);
2.4–2.6 (2H, m); 2.6–2.9 (2H, m);
5.30 (1H, s); 7.50 (1H, d);
7.90 (1H, d); 8.00 (1H, d).

EXAMPLE 9

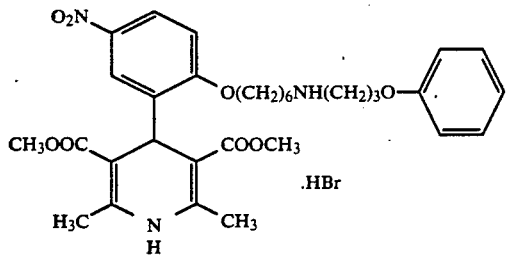

Dimethyl 4-[2-[4-(3-phenoxypropylamino)hexyloxy]-5-nitrophenyl]-2,6-dimethyl-1,4-dihydropyridine-3,5-dicarboxylate hydrobromide Physicochemical Properties (i) Melting point: 197°–198° C.

| (ii) Elementa analysis (as $C_{32}H_{42}N_3O_8Br$) | | | |
|---|---|---|---|
| | C (%) | H (%) | N (%) |
| Calcd. | 56.81 | 6.26 | 6.21 |
| Found | 57.20 | 6.25 | 6.33 |

(iii) Nuclear magnetic resonance (DMSO-$d_6$)
δ: 1.3–2.3 (8H, m); 2.28 (6H, s);
2.8–3.4 (4H, m); 6.50 (6H, s);
4.0–4.2 (4H, m); 5.22 (1H, s);
6.8–7.4 (6H, m); 7.9–8.1 (2H, m).

EXAMPLE 10

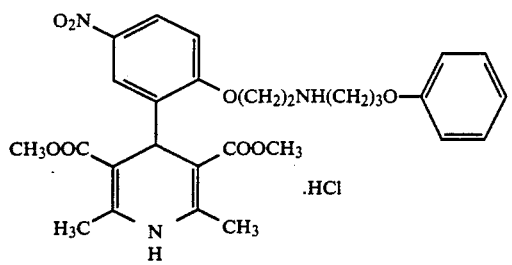

Dimethyl 4-[2-[4-(3-phenoxypropylamino)ethoxy]-5-nitrophenyl]-2,6-dimethyl-1,4-dihydropyridine-3,5-dicarboxylate hydrochloride Physicochemical Properties (i) Melting point: 118°–120° C.

| (ii) Elemental analysis (as $C_{28}H_{34}N_3O_8Cl$) | | | | |
|---|---|---|---|---|
| | C (%) | H (%) | N (%) | Cl (%) |
| Calcd. | 58.38 | 5.95 | 7.29 | 6.15 |
| Found | 58.55 | 5.87 | 7.17 | 6.54 |

(iii) Nuclear magnetic resonance (DMSO-$d_6$)
δ: 2.28 (6H, s); 3.2–3.6 (12H, m);
4.12 (2H, t); 4.5 (2H, t);
5.26 (1H, s); 6.8–7.5 (6H, m);
8.0–8.2 (2H, m).

EXAMPLE 11

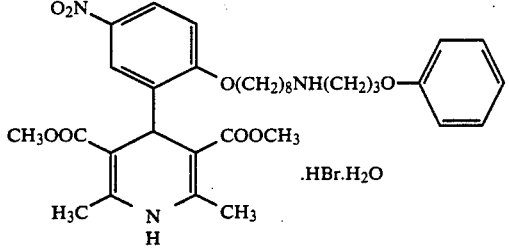

Dimethyl 4-[2-[4-(3-phenoxypropylamino)octyloxy]-5-nitrophenyl]-2,6-dimethyl-1,4-dihydropyridine-3,5-dicarboxylate hydrobromide monohydrate Physicochemical Properties (i) Amorphous powders

| (ii) Elemental analysis (as $C_{34}H_{48}N_3O_9Br$) | | | |
|---|---|---|---|
| | C (%) | H (%) | N (%) |
| Calcd. | 60.66 | 6.96 | 6.24 |
| Found | 60.68 | 6.96 | 6.26 |

(iii) Nuclear magnetic resonance (DMSO-$d_6$)
δ: 1.2–1.9 (8H, m); 2.0–2.4 (6H, m);
2.7–3.2 (4H, m); 3.52 (6H, s);
4.08 (4H, t); 5.24 (1H, s);
6.29–7.4 (6H, m); 7.9–8.1 (2H, m);
8.04 (1H, s).

EXAMPLE 12

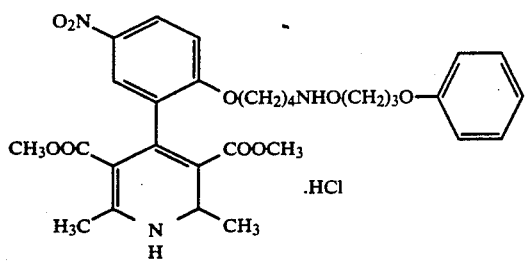

Dimethyl 4-[2-[4-(3-phenoxypropylamino)butoxy]-5-nitrophenyl]-2,6-dimethyl-1,4-dihydropyridine-3,5-dicarboxylate hydrochloride Physicochemical Properties (i) Melting point: 155°–158° C.

| (ii) Elemental analysis (as $C_{30}H_{38}N_3O_9Cl$) | | | | |
|---|---|---|---|---|
| | C (%) | H (%) | N (%) | Cl (%) |
| Calcd. | 58.11 | 6.18 | 6.78 | 5.72 |
| Found | 57.92 | 6.12 | 6.79 | 5.45 |

(iii) Nuclear magnetic resonance (DMSO-$d_6$)
δ: 1.6–2.3 (6H, m); 2.28 (6H, s);
3.3–3.6 (2H, m); 3.50 (6H, s);
3.9–4.2 (6H, m); 5.20 (1H, s);
6.8–7.4 (6H, m); 7.9–8.2 (2H, m);
9.08 (1H, s).

EXAMPLE 13

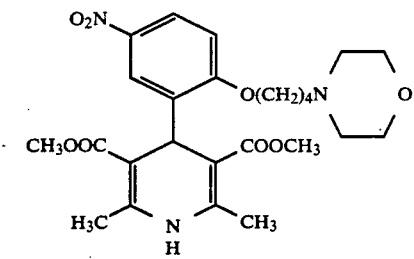

Dimethyl 4-[2-[4-(morpholino)butoxy]-5-nitrophenyl]-2,6-dimethyl-1,4-dihydropyridine-3,5-dicarboxylate Physicochemical Properties (i) Melting point: 195°–197° C.

| (ii) Elemental analysis (as $C_{25}H_{33}N_3O_8$) | | | |
|---|---|---|---|
| | C (%) | H (%) | N (%) |
| Calcd. | 59.63 | 6.61 | 8.34 |
| Found | 59.45 | 6.60 | 8.00 |

(iii) Nuclear magnetic resonance (CDCl$_3$)
δ: 1.4–2.0 (4H, m); 2.0–2.6 (10H, m);
3.3–3.8 (10H, m); 4.12 (2H, t);
5.24 (1H, s); 7.10 (1H, d);
7.9–8.1 (2H, m).

EXAMPLE 14

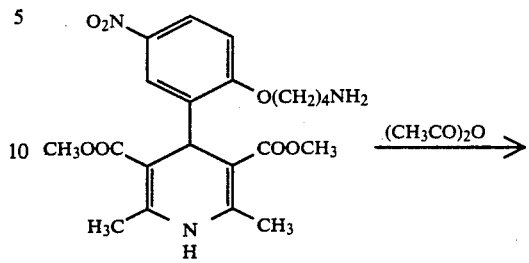

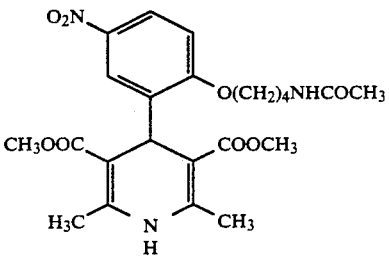

In 2 ml of methylene chloride was dissolved 0.31 g of dimethyl 4-[2-(4-aminobutoxy)-5-nitrophenyl]-2,6-dimethyl-1,4-dihydropyridine-3,5-dicarboxylate. After 2 ml of acetic anhydride was added to the solution under ice cooling, the mixture was stirred for 30 minutes at room temperature. The reaction solution was concentrated under reduced pressure and ether was added to the residue to solidify. The solid was recrystallized from chloroform-n-hexane to give 0.26 g of dimethyl 4-[2-[4-(acetylamino)butoxy]-5-nitrophenyl]-2,6-dimethyl-1,4-dihydropyridine-3,5-dicarboxylate.
This compound has the following physicochemical properties.

(i) Melting point: 212°–231° C.

| (ii) Elemental analysis (as $C_{23}H_{29}N_3O_8$) | | | |
|---|---|---|---|
| | C (%) | H (%) | N (%) |
| Calcd. | 58.10 | 6.15 | 8.84 |
| Found | 57.67 | 6.01 | 8.74 |

EXAMPLE 15

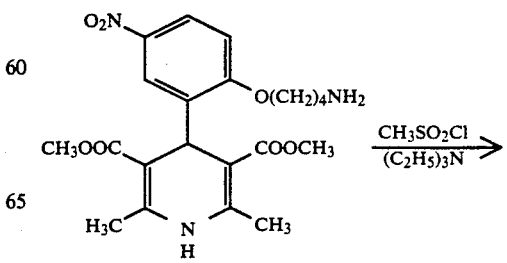

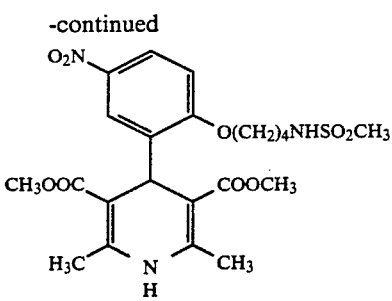

In 4 ml of methylene chloride was dissolved 0.43 g of dimethyl 4-[2-(4-aminobutoxy)-5-nitrophenyl]-2,6-dimethyl-1,4-dihydropyridine-3,5-dicarboxylate. After 0.138 ml of triethylamine and 0.077 ml of methanesulfonyl chloride were added to the solution under ice cooling, the mixture was stirred for 3 days at room temperature. To the reaction solution were added 50 ml of ethyl acetate and 20 ml of 2N hydrochloride to fractionate the organic phase. The solvent was removed by distillation under reduced pressure. The obtained residue was subjected to silica gel column chromatography and eluted by chloroform:methanol (9:1 v/v). The obtained crude crystals were crystallized from chloroform-n-hexane to give 0.31 g of dimethyl 4-[2-(4-methanesulfonylamino)butoxy)-5-nitrophenyl]-2,6-dimethyl-1,4-dihydropyridine-3,5-dicarboxylate. This compound has the following physicochemical properties.

(i) Melting point: 213°–216° C.

| (ii) Elemental analysis (as $C_{22}H_{29}N_3O_9S.\frac{1}{2}H_2O$) | | | |
|---|---|---|---|
| | C (%) | H (%) | N (%) |
| Calcd. | 50.76 | 5.81 | 8.07 |
| Found | 50.09 | 5.44 | 7.83 |

EXAMPLE 16

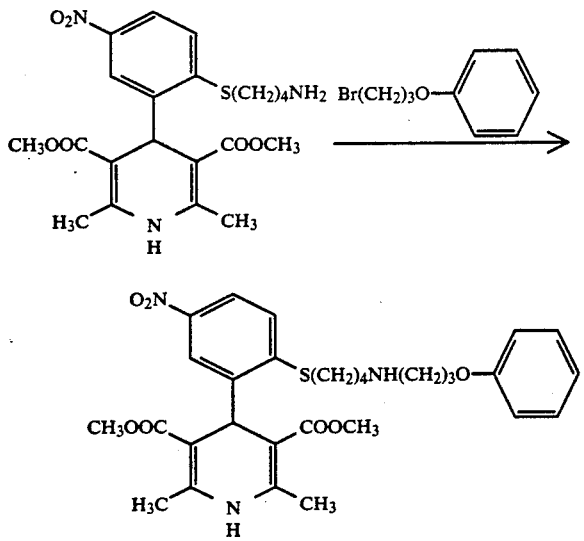

In 30 ml of acetonitrile were dissolved 1.35 g of dimethyl 4-[2-(4-aminobutylthio)-5-nitrophenyl]-2,6-dimethyl-1,4-dihydropyridine-3,5-dicarboxylate obtained in Reference Example 2 and 0.645 g of 1-bromo-3-phenoxypropane. The solution was heated to reflux for 30 minutes. The solvent was removed by distillation under reduced pressure. The obtained residue was subjected to silica gel column chromatography and eluted by chloroform:methanol (9:1 v/v). The obtained yellow oily substance was converted into the hydrochloride with hydrochloric acid-ethanol. By drying under reduced pressure, 0.37 g of dimethyl 4-[2-[4-(3-phenoxypropylamino)butylthio]-5-nitrophenyl[-2,6-dimethyl-1,4-dihydropyricine-3,5-dicarboxylate hydrochloride. This compound has the following physicochemical properties.

(i) Amorphous powders

| (ii) Elemental analysis (as $C_{30}H_{38}N_3O_7SCl$) | | | |
|---|---|---|---|
| | C (%) | H (%) | N (%) |
| Calcd. | 58.10 | 6.18 | 6.78 |
| Found | 58.24 | 6.13 | 6.62 |

(iii) Nuclear magnetic resonance (DMSO-$d_6$)
$\delta$: 1.6–2.0 (6H, m); 2.24 (6H, s); 2.5–3.3 (6H, m); 3.50 (6H, s); 4.60 (2H, t); 5.30 (1H, s); 7.92 (1H, d); 7.96 (1H, bs); 6.8–7.6 (6H, m); 9.12 (1H, bs).

EXAMPLE 17

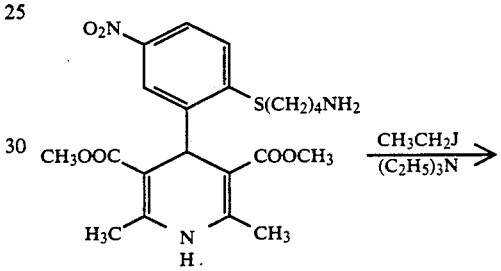

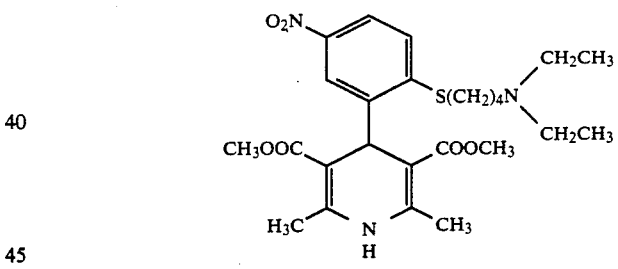

In 10 ml of acetonitrile were dissolved 0.45 g of dimethyl 4-[2-(4-aminobutylthio)-5-nitrophenyl]-2,6-dimethyl-1,4-dihydropyridine-3,5-dicarboxylate, 0.16 g of ethyl iodide and 0.10 g of triethylamine. The solution was heated to reflux for 30 minutes. The solvent was removed by distillation under reduced pressure. The obtained residue was subjected to silica gel column chromatography and eluted with ammonia-saturated chloroform:isopropyl alcohol (9:1 v/v). The obtained yellow oily substance was converted into the hydrochloride with hydrochloric acid-ethanol. By drying under reduced pressure, 0.19 g of dimethyl 4-[2-(4-diethylaminobutylthio))-5-nitrophenyl]-2,6-dimethyl-1,4-dihydropyridine-3,5-dicarboxylate hydrochloride. This compound has the following physicochemical properties.

(i) Amorphous powders

| (ii) Elemental analysis (as $C_{25}H_{36}N_3O_6SCl$) | | | |
|---|---|---|---|
| | C (%) | H (%) | N (%) |
| Calcd. | 55.39 | 6.69 | 7.75 |

-continued

| (ii) Elemental analysis (as $C_{25}H_{36}N_3O_6SCl$) | | |
|---|---|---|
| C (%) | H (%) | N (%) |
| Found 55.74 | 6.49 | 7.69 |

(iii) Nuclear magnetic resonance (DMSO-$d_6$)
δ: 1.42 (6H, t); 1.6–2.3 (4H, m);
2.40 (6H, s); 2.8–3.4 (8H, m);
3.56 (6H, s); 5.42 (1H, bs);
7.10 (1H, d); 7.90 (1H, d);
8.20 (1H, d).

We claim:

1. A 1,4-dihydropyridine derivative represented by Formula (I):

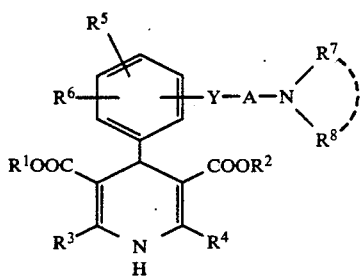

wherein:
$R^1$ and $R^2$, which may be the same or different, each represents a $C_1$–$C_{10}$ alkyl group which may be interrupted by an oxygen atom, a $C_3$–$C_6$ cycloalkyl-substituted lower alkyl group or a halogen-substituted lower alkyl group;
$R^3$ and $R^4$, which may be the same or different, each represent a lower alkyl group;
$R^5$ and $R^6$, which may be the same or different, each represent a hydrogen atom, a nitro group, a halogen atom, a lower alkyl group, a lower alkoxy group, a lower alkylthio group, a lower alkylsulfonyl group or a lower alkylsulfinyl group;
$R^7$ represents a hdyrogen atom or a lower alkyl group;
$R^8$ represents a methoxy lower alkyl group, a hydroxy-lower alkyl group, a phenyl-lower alkyl group, naphthyl-lower alkyl group, a phenyl gruop, a naphthyl group, a lower alkanoyl group or a lower alkylsulfonyl group, provided that $R^7$ and $R^8$ may be combined together with a nitrogen atom(s) to form a pyrrole ring, a piperidine ring, a morpholine ring a piperazine ring azepine ring, unsubstituted or substituted with a lower alkyl group, a phenyl-lower alkyl group or a haphthyl-lower alkyl group;
A represents a $C_1$–$C_{12}$ alkylene group, a $C_2$–$C_{12}$ alkenylene group or a $C_2$–$C_{12}$ alkynylene group; and
Y represents an oxygen atom or a sulfur atom, or a salt thereof.

2. A pharmaceutical composition useful as a calcium antagonist and comprised of a therapeutically effective amount of a 1,4-dihydropyridine derivative represented by the Formula (I):

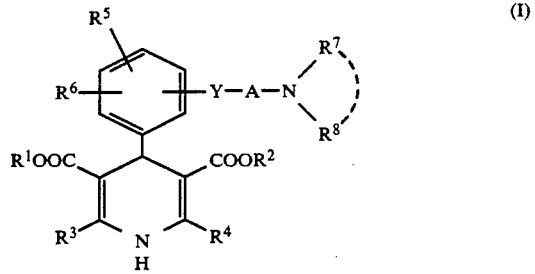

wherein
$R^1$ and $R^2$, which may be the same or different, each represent a $C_1$–$C_{10}$ alkyl group which may be intervened by an oxygen atom, a $C_3$–$C_6$ cycloalkyl-substituted lower alkyl group or a halogen-substituted lower alkyl group;
$R^3$ and $R^4$, which may be the same or different, each represent a lower alkyl group;
$R^5$ and $R^6$, which may be the same or different, each represent a hydrogen atom, a nitro group, a halogen atom, a lower alkyl group, a lower alkoxy group, a lower alkylthio group, a lower alkylsulfonyl group or a lower alkylsulfinyl gruop;
$R^7$ represents a hydrogen atom or a lower alkyl group;
$R^8$ represents a methoxy lower alkyl group, a hydroxy-lower alkyl group, a phenyl-lower alkyl group, a naphthyl-lower alkyl group, a phenyl group, a naphthyl group, a lower alkanoyl group or a lower alkylsulfonyl group, provided that $R^7$ and $R^8$ may be combined together with a nitrogen atom(s) to form a pyrrole ring, a piperidine ring, a morpholine ring, a piperazine ring an azepine ring, unsubstituted or substituted with a lower alkyl group, a phenyl-lower alkyl group or a naphthyl-lower alkyl group;
A represents a $C_1$–$C_{12}$ alkylene group, a $C_2$–$C_{12}$ alkenylene group or a $C_1$–$C_{12}$ alkynylene group; and
Y represents an oxygen atom or a sulfur atom, or a salt thereof, and a pharmaceutically acceptable carrier.

3. A method for imparting calcium antagonistic activity in a subject which comprises administering to said subject a calcium antagonistic effective amount of the pharmaceutical composition of claim 2.

* * * * *